(12) United States Patent
Levinos et al.

(10) Patent No.: US 6,511,221 B1
(45) Date of Patent: Jan. 28, 2003

(54) APPARATUS FOR MEASURING THERMOMECHANICAL PROPERTIES OF PHOTO-SENSITIVE MATERIALS

(75) Inventors: Nicholas James Levinos, Hampton, NJ (US); Stephen Reid Popielarski, Narberth, PA (US)

(73) Assignee: Agere Systems Inc., Miami Lakes, FL (US)

( * ) Notice: Subject to any disclaimer, the term of this patent is extended or adjusted under 35 U.S.C. 154(b) by 0 days.

(21) Appl. No.: 09/420,234

(22) Filed: Oct. 19, 1999

(51) Int. Cl.[7] .............................. G01N 25/00
(52) U.S. Cl. ........................................ 374/45
(58) Field of Search ..................... 374/45, 43, 46–57

(56) References Cited

U.S. PATENT DOCUMENTS

| | | | | |
|---|---|---|---|---|
| 4,095,461 A | * | 6/1978 | Starita | 374/47 |
| 4,377,001 A | * | 3/1983 | Takeda et al. | 374/17 |
| 4,425,810 A | * | 1/1984 | Simon et al. | 374/45 |
| 4,481,418 A | * | 11/1984 | Vanzetti et al. | 250/338.1 |
| 4,874,948 A | * | 10/1989 | Cielo et al. | 374/53 |
| 4,896,973 A | * | 1/1990 | Hill et al. | 374/56 |
| 5,306,641 A | * | 4/1994 | Saccocio | 436/85 |
| 5,450,196 A | * | 9/1995 | Turner | 356/346 |

FOREIGN PATENT DOCUMENTS

| | | | | |
|---|---|---|---|---|
| SU | 785702 | * | 12/1980 | 374/45 |
| SU | 953566 | * | 8/1982 | 374/45 |

* cited by examiner

Primary Examiner—Diego Gutierrez
Assistant Examiner—Stanley J. Pruchnic, Jr.
(74) Attorney, Agent, or Firm—Cohen, Pontani, Lieberman & Pavane

(57) ABSTRACT

An apparatus for measuring thermomechanical properties of a photo-sensitive material sample during exposure of the sample material to a light source includes a sample holder having a sample support positionable in a sample holding area of the sample holder for holding the photo-sensitive material sample, a probe disposable relative to the sample support for measuring the thermomechanical properties of the photo-sensitive material sample, a temperature control unit having a cavity for receiving the sample holder and for maintaining the sample holder within a selectively-controlled temperature range, and an illuminating assembly operatively arranged for directing a light signal onto the sample holder for illuminating the photo-sensitive material held on the sample holder.

8 Claims, 7 Drawing Sheets

APPARATUS FOR MEASURING THERMOMECHANICAL PROPERTIES OF PHOTO-SENSITIVE MATERIALS

BACKGROUND OF THE INVENTION

1. Field of the Invention

The present invention relates to an apparatus for determining thermomechanical properties of a photo-sensitive material during exposure to light.

2. Description of the Related Art

Modern production and manufacturing processes require that materials be characterized with respect to physical properties such as glass transition, modulus (stiffness), thermal expansion, and shrinkage (during a cure, for example) to maximize the efficiency of the process and the consistency of the final product to meet required application specifications. Thermal analysis of materials involves various methods for measuring these and other physical and/or chemical properties of a material as a function of temperature. Instruments such as dynamic mechanical analyzers (DMAs) and thermomechanical analyzers (TMAs) may be used to obtain this information.

A typical prior art thermal analysis system is shown in FIGS. 7 and 8. A sample tube 1 has a sample holding area 3 at a bottom end of the sample tube. A sample 5 to be tested is mounted in the sample holding area 3 and a probe 7 is inserted through a top of the sample tube 1 to the sample area to perform a test on the sample 5. The specific configuration shown in FIG. 7 is a 3-point bending test configuration and the sample 5 is a bar. Instead of a bar, the geometry of the sample 5 may be that of a film, fiber, rod, cylinder, disk or liquid. Furthermore, instead of a 3-point bending configuration, the test configuration or measuring system may include 2- and 4-point bending, single and dual cantilever, film extension, fiber extension, or parallel plates. For all combinations of test configurations and samples, a force is applied to the sample 5 via the probe 7.

As shown in FIG. 8, the bottom end of the sample tube 1—i.e. the sample holding area 3—is inserted in a cavity 13 in a temperature control unit 9—i.e. a furnace or refrigeration unit—to control the temperature of the sample 5 during the characterization test. A split-ring ceramic insulator 11 is mounted around the sample tube 1 at the entrance area to the cavity 13 for closing the temperature control unit 9 during operation and for reducing heat loss and/or gain during its operation. FIG. 8 also shows a thermocouple 15 in the sample tube 1 and a locking nut 17 and locking mechanism 19 for holding the sample tube 1 in place during the test. The locking nut 17 and locking mechanism 19 are protected by a cover 21. A specific example of this type of instrument is a Perkin-Elmer DMA 7 Dynamic Mechanical Analyzer.

This prior art device operates very well for most samples. However, it is not possible to characterize the mechanical properties of a photo-sensitive material throughout its exposure to a light source, while accurately controlling temperature. The configuration of the temperature control unit prevents the illumination of the sample. Accordingly, a sample can not be illuminated in this prior art device while the sample tube is in the temperature control unit.

SUMMARY OF THE INVENTION

An apparatus for measuring thermomechanical properties of a photo-sensitive material sample during exposure to light such, for example, as during a photo-induced cure, according to the present invention, includes a sample holder having a sample support positionable in a sample holding area of the sample holder for holding the photo-sensitive material sample, a probe disposable relative to the sample support for measuring the thermomechanical properties of the photo-sensitive material sample, a temperature control unit having a cavity for receiving the sample holder and maintaining the sample holder within a controlled temperature range, and a lighting assembly operatively arranged for directing a light signal into the sample holder for illuminating the photo-sensitive material.

The lighting assembly may comprise a light source directed into a portal or other opening in the sample tube arranged at a location of the sample tube which is not insertable into the temperature control unit. Furthermore, a mirror or a light diffuser may be arranged in the sample tube to ensure that the sample is uniformly illuminated.

Alternatively, the lighting assembly may comprise a light source located in the temperature control unit.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views.

DETAILED DESCRIPTION OF THE CURRENTLY PREFERRED EMBODIMENTS

Figure 1A:
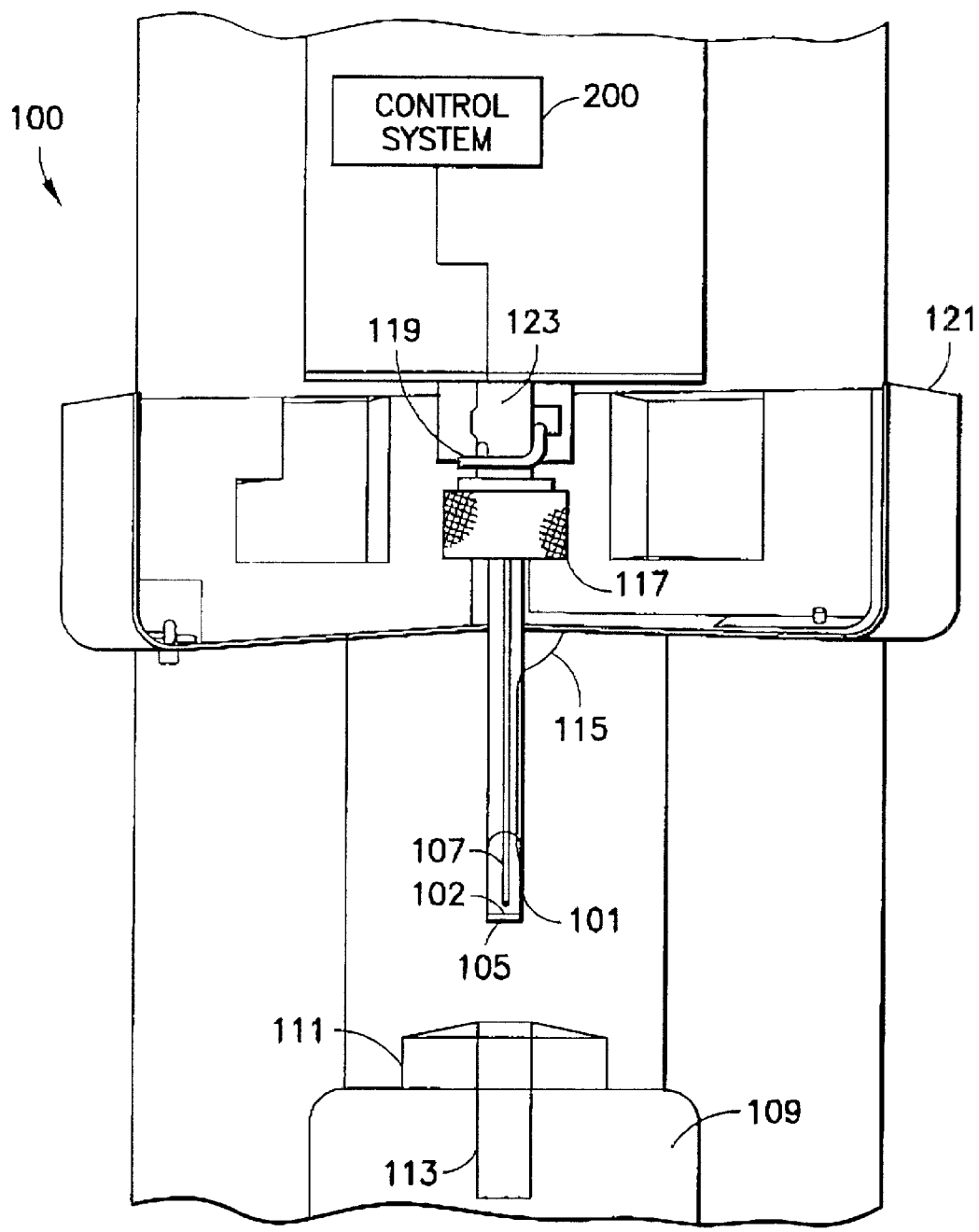
FIG. 1a is a sectional view of the main components of a device for measuring thermomechanical properties of photo-sensitive materials according to an embodiment of the present invention.

FIG. 1a depicts an apparatus 100 for measuring thermomechanical properties of a photosensitive material. A sample tube 101 includes a sample support 102 for holding at the bottom of the sample tube a sample to be tested. A probe 107 runs through the sample tube 101 from the top to the bottom for determining any physical characteristics such, for example, as shrinkage or expansion of the sample which occurs during exposure of the sample to light. As is known in the art, the geometry of the sample may be, by way of example, that of a bar, a film, a fiber, a rod, a cylinder, a disk or a liquid. The apparatus 100 may comprise a thermal analysis device which is arrangable in many test configurations including 2, 3, and 4-point bending, single and dual cantilever, film extension, fiber extension, or parallel plates for determining various characteristics of a sample such as glass transition, modulus (stiffness), thermal expansion, and shrinkage. For all combinations of test configurations and samples, a force may be applied to the sample via the probe 107. However, for determining physical characteristics of a sample 105 during a photo-cure, the probe 107 rests on the sample under the smallest possible load necessary to hold the probe against the sample during the exposure of the sample to light. The size of the smallest load is dependent on the capabilities of a control system 200 (shown schematically in FIG. 1a) that controls the position of probe 1–7 and the type of sample being tested. For example, a solid sample can withstand a much higher load than a liquid sample.

The bottom end of sample tube 101—in which the sample is housed—is inserted in a cavity 113 of a temperature control unit 109, which may comprise a furnace for heating the sample and/or a refrigeration unit for cooling the sample, for controlling the temperature of the sample during the characterization test. An insulating device such as a split-ring ceramic insulator 111 or any other type of insulating device is mounted around the sample tube 101 at the entrance area of the cavity 113 for closing the temperature control unit 109 during operation and reducing heat loss and/or gain during its operation. A thermocouple 115 is inserted in the sample tube for measuring the temperature proximate the sample during operation. The output of the thermocouple may be connected to monitoring devices and/or to a control unit that controls the temperature control unit 109. A locking nut 117 and locking mechanism 119 connect the sample tube 101 to a core rod 123 which holds the sample tube. The temperature control unit is movable so that it can be raised toward the sample tube. The core rod 123 may also be controlled via the control system 200. The locking nut 117 and locking mechanism 119 are protected by a cover 121. Instead of the temperature control unit 109 depicted in FIG. 1, the temperature control unit 109 may be a larger temperature controlled area in which the sample tube is placed such, as a temperature enclosed area under a hood or a temperature controlled room.

Figure 1B:
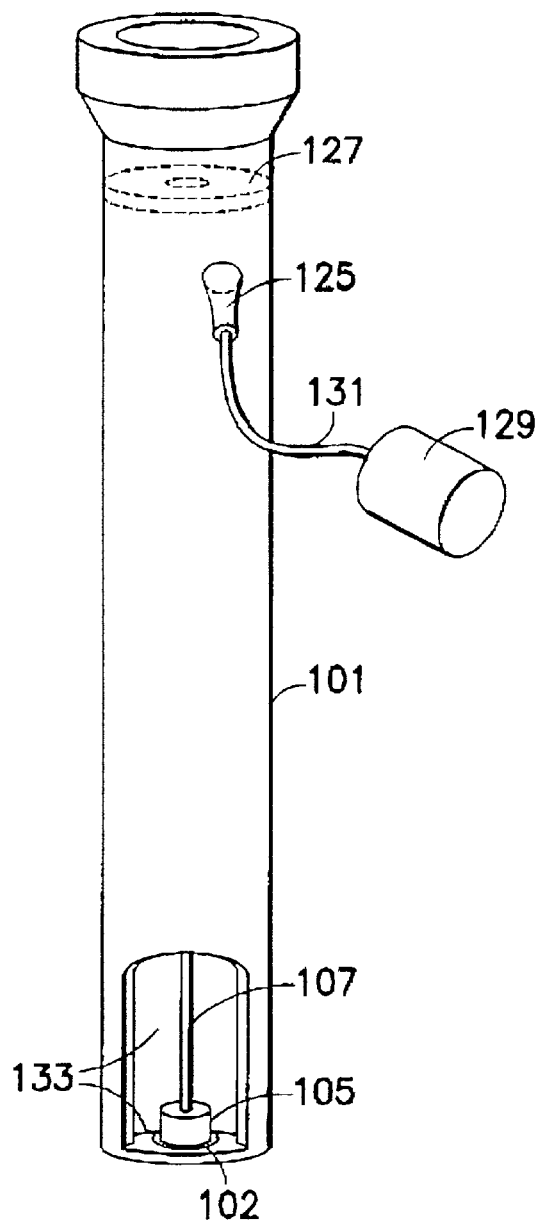
FIGS. 1b and 1c are front and side views of a sample tube used for holding the photo-sensitive material in the device of FIG. 1a and having an upward-directed portal for receiving a light source.
Figure 1C:
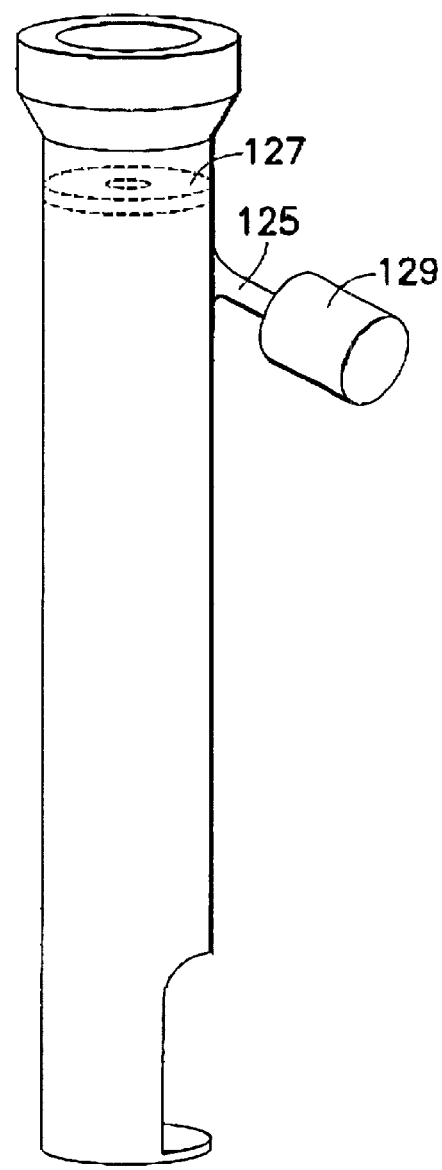

FIGS. 1b and 1c show the sample tube 101 of FIG.1a which may be used for determining the thermomechanical properties of a photo-sensitive sample 105 (shown schematically in FIG. 1b) throughout and exposure to light. To accomplish this, the sample tube 101 includes a portal 125 through which light emanating from a light source 129 is directed. Furthermore, a mirror 127 is mounted at the upper end of sample tube 101 for reflecting the incoming light downward toward the sample 105. The mirror 127 has a hole in its center to allow the probe 107 to move therethrough. As seen in FIG. 1b, the light from light source 129 may be directed to portal 125 through an optical fiber 131. As an alternative, light source 129 may be mounted so that its output is transmitted directly into portal 125 (see FIG. 1c). In a preferred embodiment, the sample support 102 and probe comprise quartz. This quartz measuring system allows at least some UV light to be transmitted therethrough, thereby allowing the entire smaple to be illuminated. If a visible light source is used, the sample support 102 and probe 107 may comprise other materials that are substantially transparent to visible light and can withstand the test temperatures such, for example, as glass. To further ensure that the sample 105 is uniformly illuminated, the interior walls of the sample tube 101 are coated with a reflective coating 133 such, for example, as aluminum.

Figure 2:
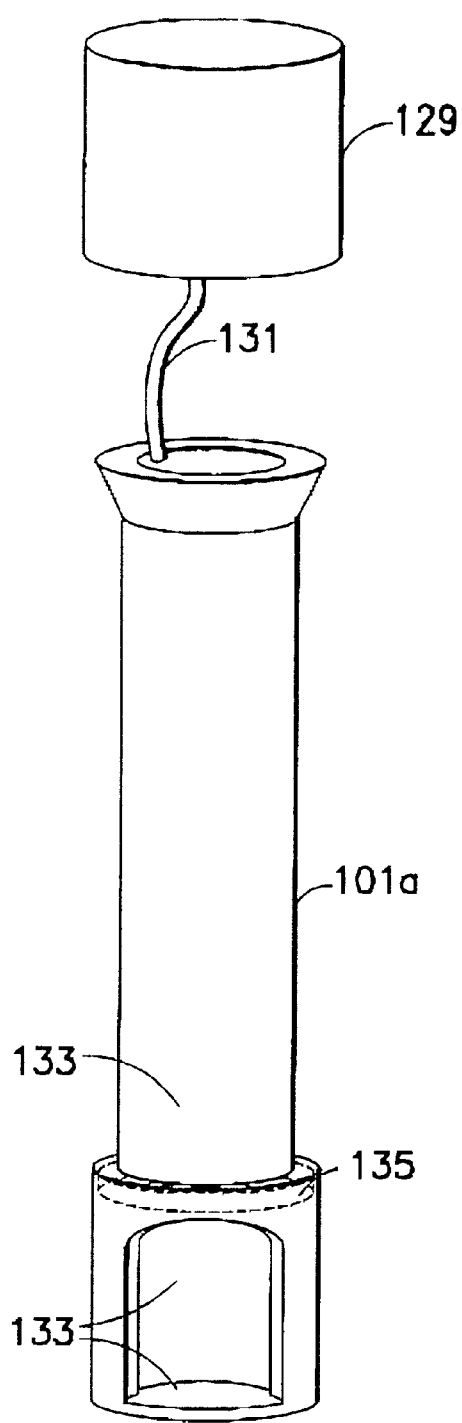
FIG. 2 is a front view of a sample tube having a light source mounted above the top of the sample tube.

FIG. 2 depicts a sample tube 101a according to a further embodiment of the invention in which the light source 129 is directed through the upper portion of the sample tube 101a. Instead of a mirror, sample tube 101a may include a light diffuser 135 for scattering the light so that the sample is uniformly illuminated. The light diffuser 135 must also have a hole allowing the probe 107 to move therethrough. This embodiment may also include a reflective coating 133 on the interior walls.

Figure 3:
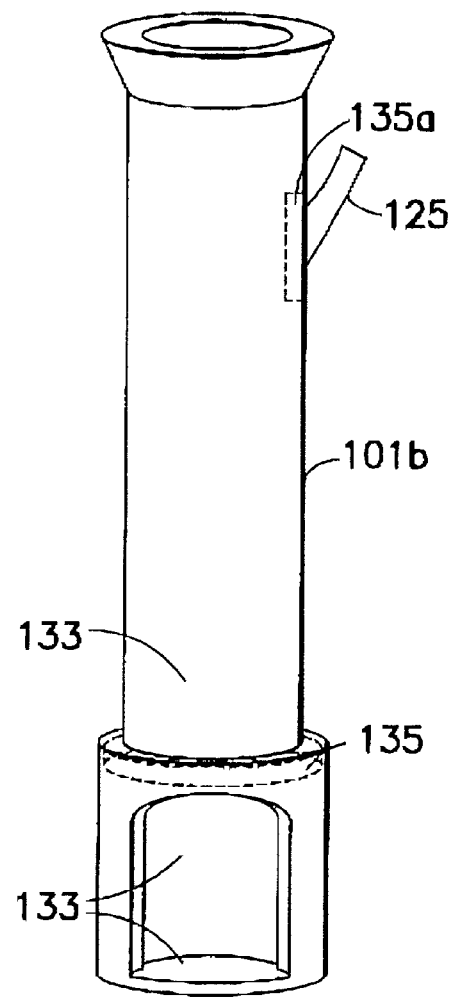
FIG. 3 is a front view of a sample tube having a downward-directed portal for receiving a light source.

FIG. 3 illustrates yet another sample tube 101b to which a downwardly-directed portal 125 is attached. This embodiment includes a reflective coating 133 on the interior walls of the sample tube 101b and may further include a light diffuser 135 for scattering the light (as in the embodiment of FIG. 2) to more uniformly illuminate the sample 105. Instead of light diffuser 135, a light diffuser 135a may be mounted at the interior end of the portal to scatter the light as it enters the sample tube 101b.

Figure 4:
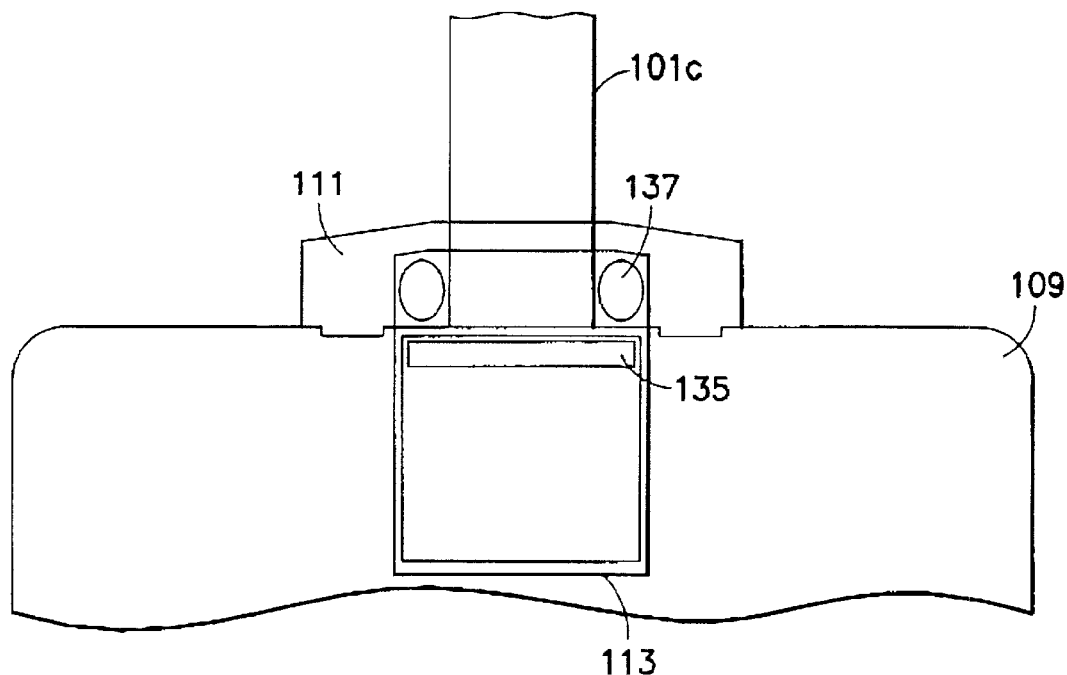
FIG. 4 depicts a portion of a sample tube inserted into a temperature control unit according to another embodiment of the present invention.
Figure 5A:
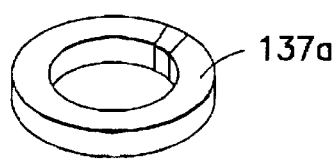
FIGS. 5a and 5b are perspective views of two different light sources which may be used to illuminate a sample in the configuration of FIG. 4.
Figure 5B:
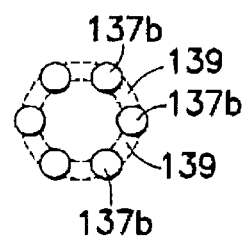

In the embodiment of FIG. 4, an annular light source 137 is mounted in the ceramic insulation ring 111. In this embodiment, the lower end of a sample tube 101c is of slightly larger width or cross-section or diameter than the remainder of the sample tube. The annular light source is arranged so that it transmits the light into the lower end of tube 101c through the edge defined between the increased-width lower section and the remainder of the sample tube. As shown in FIG. 5a, the annular light source may comprise a single-piece light source 137a in which the light source itself is annular-shaped or, alternatively, a plurality of smaller light sources annularly arranged and connected via connectors 139, as shown in FIG. 5b. Regardless of the type of annular light source 137, a light diffuser 135 may be included to scatter the light so that a sample is uniformly illuminated. Alternatively, or in addition to light diffuser 135, a reflective coating 133 may be applied to the interior walls of sample tube 101c.

Figure 6:
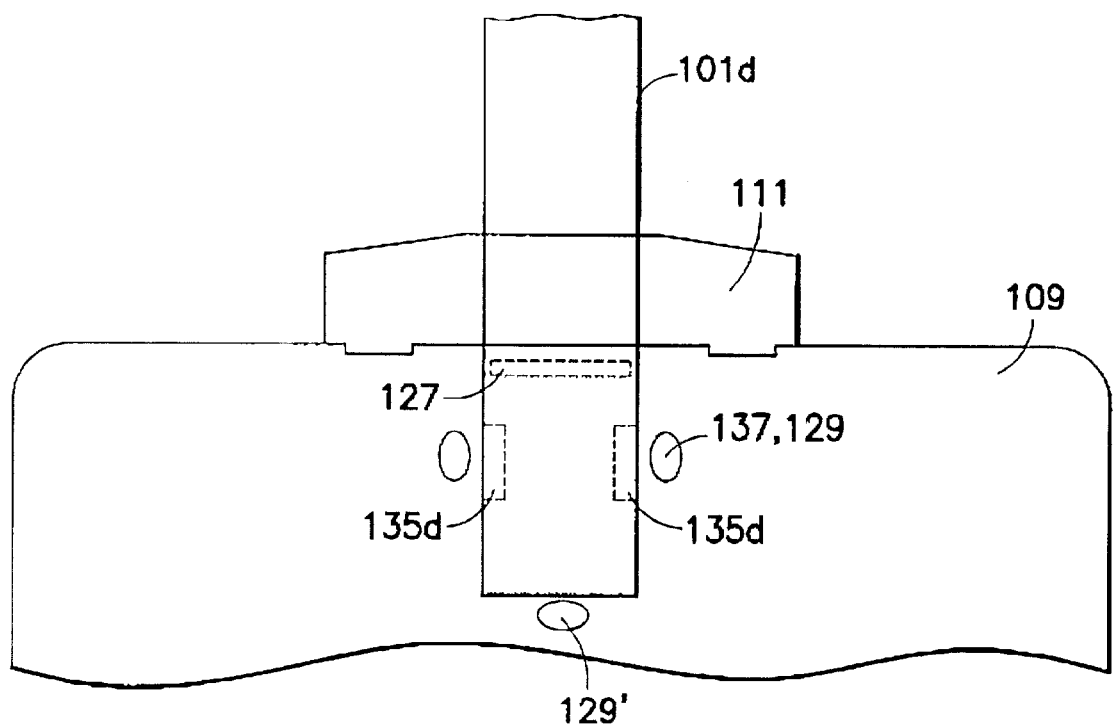
FIG. 6 is a sectional view of a sample tube and a temperature control unit as in FIG. 1 with a light source mounted in the temperature control unit.
Figure 7:
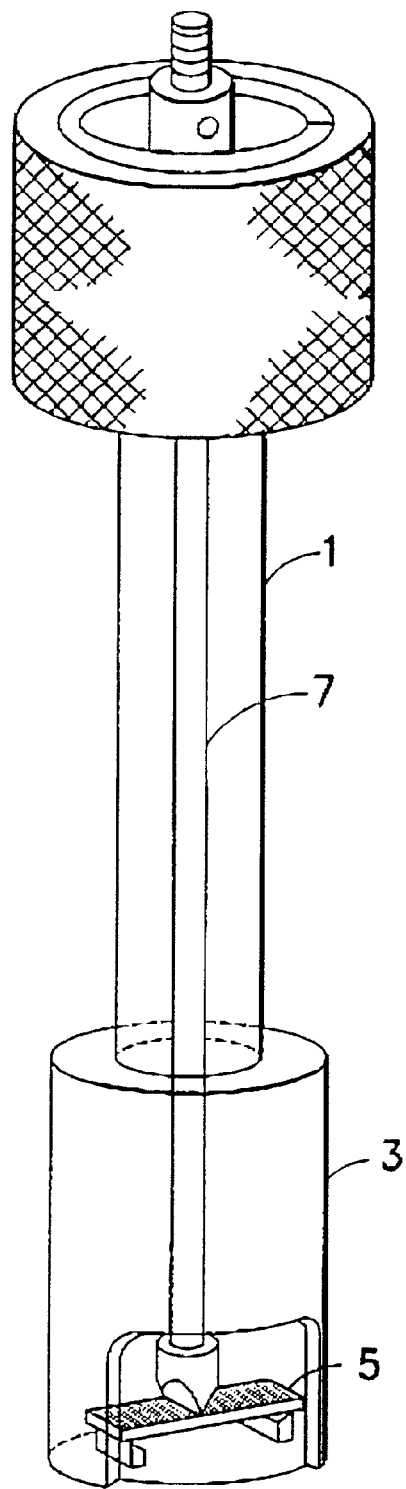
FIG. 7 is an elevated perspective view of a prior art sample tube used for thermal analysis of a sample.
Figure 8:
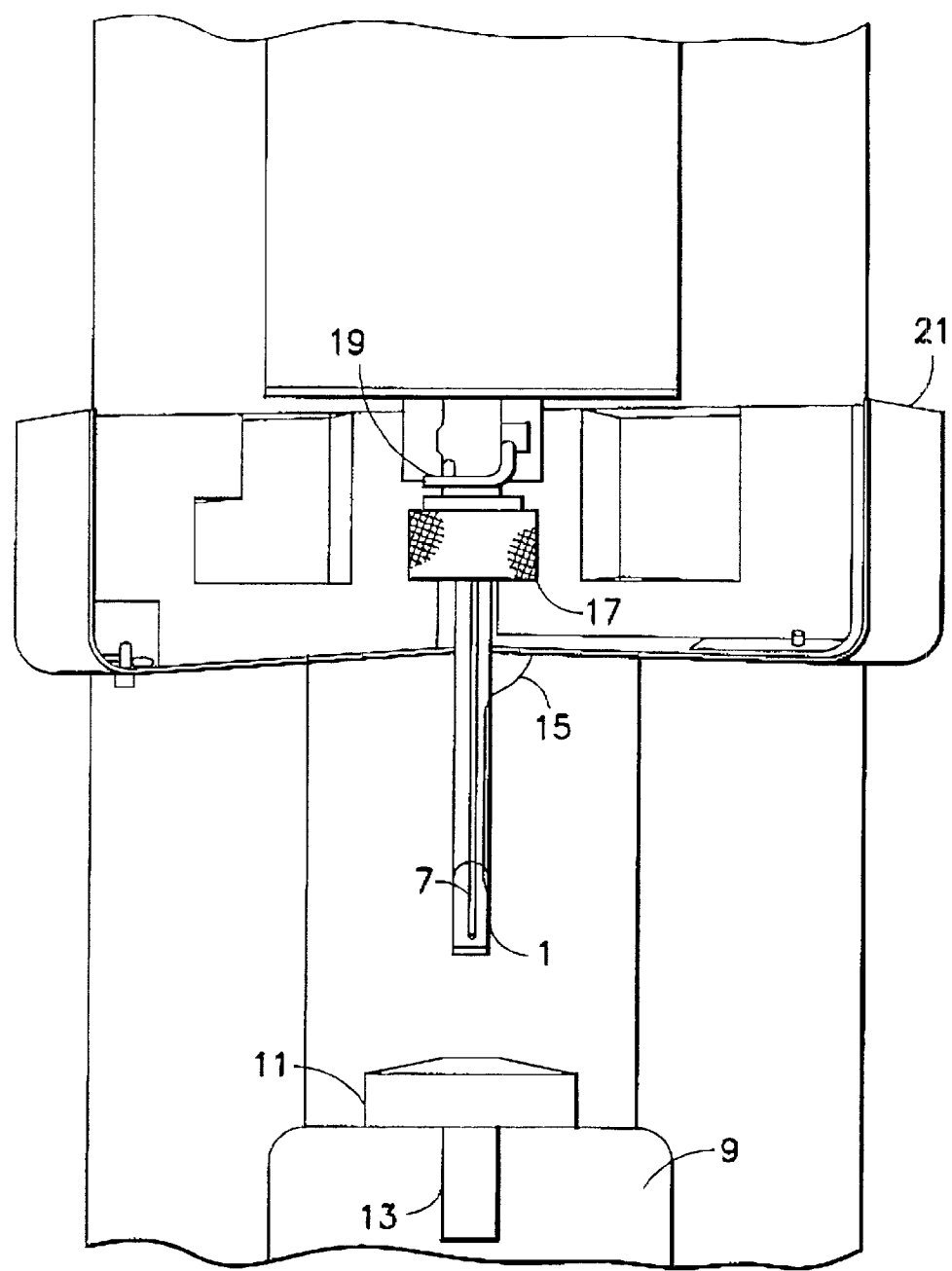
FIG. 8 is a cross-sectional view of a prior art thermal analysis system using the sample tube of FIG. 7.

FIG. 6 depicts another embodiment of the invention, in which the light source 137, 129 is mounted within the temperature control unit 109. In this embodiment, the sample tube 101d may comprise a reflective coating 133 applied to the interior walls and may further include a mirror 127 for reflecting light back toward the sample. In addition, a light diffuser 135d may be positioned in sample tube 110d at or proximate the area at which the light enters the sample tube for scattering the light to more uniformly illuminate the sample. Furthermore, a bottom light source 129' may be further arranged on a bottom of the sample tube 101d. The bottom light source 129' facilitates the total illumination of the sample including the bottom of the sample. The bottom light source 129' may be used with the light source 129, 137 or by itself. If the bottom light source 129' is used alone, the mirror 127 may be used to reflect the light onto the top of the sample if required for the particular application.

While there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An apparatus for measuring thermomechanical properties of a photo-sensitive material sample during exposure of the sample to light, comprising:

a sample holder having a sample support positionable in a sample holding area of said sample holder for holding the photo-sensitive material sample;

a probe disposable relative to said sample support for measuring the thermomechanical properties of the photo-sensitive material sample held in the sample holder;

a temperature control unit having a cavity for receiving at least a portion of said sample holder and for maintaining said sample holder portion within a selectively controlled temperature range; and an illuminating light assembly operatively arranged for directing a light beam in said sample holder for illuminating the photo-sensitive material held on said sample holder and comprising a portal defined in said sample holder and a light source for transmitting the light beam into said sample holder through said portal, wherein said portal is configured so that the light beam entering said portal is directed away from said sample holding area.

2. The apparatus of claim 1, wherein said illuminating assembly further comprises a mirror facing said sample holding area and arranged so that said portal is located between said mirror and said sample holding area.

3. The apparatus of claim 2, wherein said sample holder comprises interior surfaces and said illuminating assembly further comprises a reflective coating on a portion of said interior surfaces.

4. The apparatus of claim 1, wherein said sample holder comprises interior surfaces and said illuminating assembly further comprises a reflective coating on a portion of said interior surfaces.

5. The apparatus of claim 1, wherein said illuminating assembly further comprises an optical fiber for optically connecting said light source to said portal.

6. The apparatus of claim 1, wherein said sample holder, said probe, and said temperature control unit comprise parts of a thermal analysis machine operable for performing tests for determining physical and chemical properties of a material as a function of temperature.

7. The apparatus of claim 1, wherein the light beam is UV light and at least one of said sample support and said probe comprises quartz.

8. The apparatus of claim 1, wherein the light beam is visible and at least one of said sample support and said probe comprises glass.

* * * * *